Aug. 24, 1954 F. MEILLAND Plant Pat. 1,298
ROSE PLANT
Filed Aug. 12, 1953
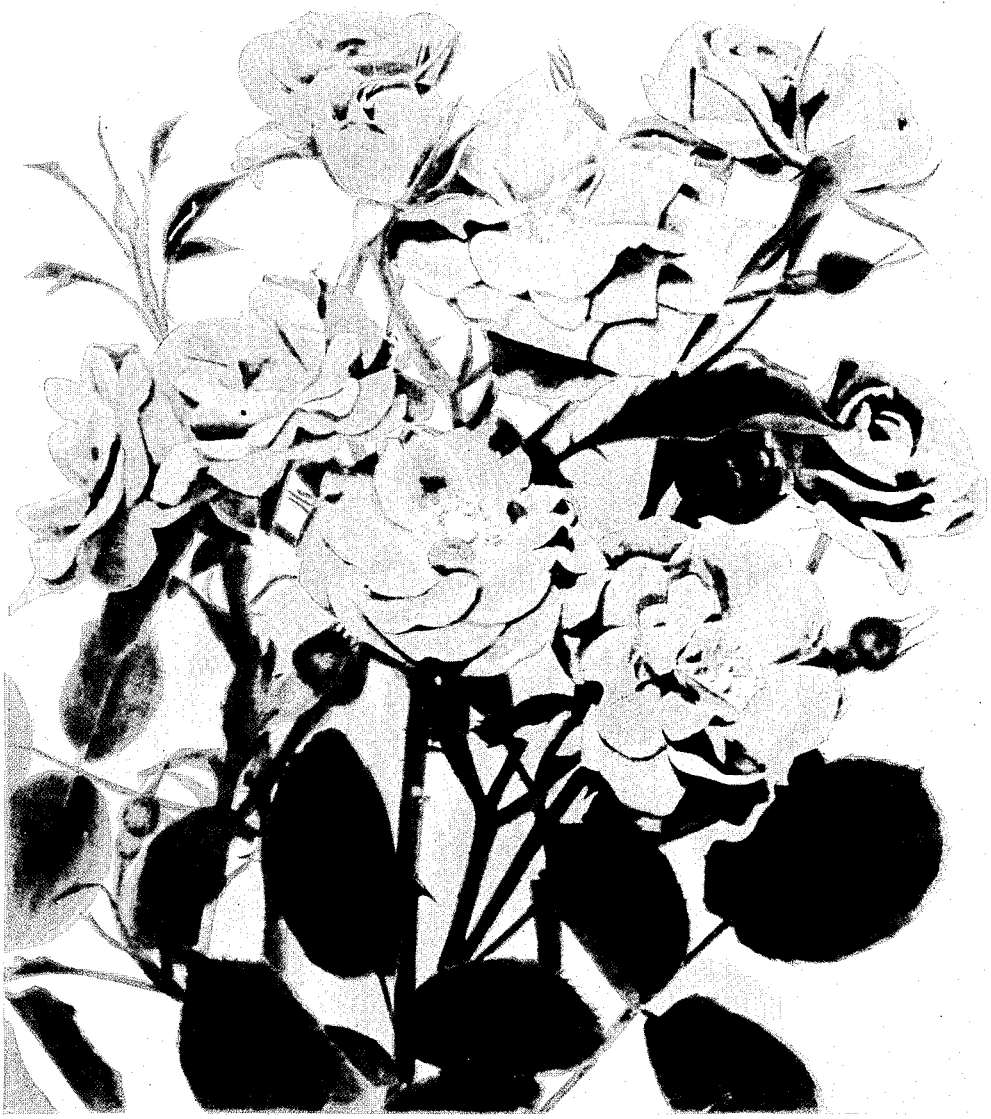
Inventor.
Francis Meilland
By: Robb & Robb
Attorneys.

Patented Aug. 24, 1954

Plant Pat. 1,298

UNITED STATES PATENT OFFICE 1,298

ROSE PLANT

Francis Meilland, Cap Azura, Cap d'Antibes, Alps Maritime, France, assignor to The Conard-Pyle Company, West Grove, Pa., a corporation of Pennsylvania Application August 12, 1953, Serial No. 373,930

Claims priority, application France August 22, 1952

1 Claim. (Cl. 47—61)

This invention relates to a new and distinct hybrid polyantha rose plant of the type commonly called floribunda rose plants, originated by me by crossing the variety "Alain" (unpatented) with the variety "Orange Triumph" (unpatented).

The new variety is distinguished from its parents, as well as from all other varieties of its class, by its extremely brilliant Flame-Rose general color tonality.

In addition to its usefulness for garden decoration, the new variety is very well-suited for the production of cut flowers under glass, and the color of the new variety is unique in the cut-flower line of commerce.

Asexual reproduction of my new variety by budding at Cap d'Antibes, France, and at West Grove, Pennsylvania, U. S. A., shows that the characteristics of this new variety come true to form and are established and transmitted through succeeding propagations.

In the accompanying drawing, there is depicted a specimen of the new variety, showing the flowers in different stages of development from new bud to fully open flower, and also showing the foliage and stems in different stages of development.

The following is a detailed description of my new variety, with color terminology in accordance with Ridgway's Color Standards and Nomenclature, except where general color terms of ordinary dictionary significance are obvious:

Type: Hardy; bush; seedling; for garden decoration and for cut-flowers.
Class: Hybrid polyantha.
Breeding: Seedling.
*Seed parent.*—"Alain."
*Pollen parent.*—"Orange Triumph."
Propagation: Holds its distinguishing characteristics through succeeding propagations by budding.

*Flower*

Locality where grown and observed: West Grove, Pennsylvania, U. S. A.
Flower borne: Several to stem; in regular rounded cluster; on normal strength, medium length stems.
Quantity of bloom: Abundant, outdoors.
Continuity: Continuous.
Fragrance: Slight.
Bud:
*Peduncle.*—Medium length; medium caliper; stiff; medium number of brown prickles.

Color—green tinged with Pompeian Red, Plate XIII.
*Before calyx breaks.* — Size — medium. Form—medium-pointed, with a conspicuous neck; with foliaceous appendages on the surface of the bud; with slender, entire foliaceous parts extending beyond the tip of the bud equal to ¾ or more of its length.
*As calyx breaks.*—Color—Ox-blood Red, Plate I at tip, shading to Scarlet, Plate I.
*As first petal opens.* — Size — medium. Form—medium length; pointed-ovoid. Color: outside—Carmine, Plate I, shading down to Pale Amaranth Pink, Plate XII at base; inside—Spectrum Red, Plate I, with narrow area of Pale Amparo Purple, Plate XI at base.
*Opening.*—Opens up well.
Bloom:
*Size (when fully open).*—Medium; 2 inches to 2¼ inches.
*Petalage.*—Semi-double; from 20 to 25 petals; arranged regularly.
*Form.*—Slightly open-cupped at first; becoming open-cupped; petals being at first loosely cupped; becoming later at maturity loosely rolled outward.
Petals: Medium thickness; leathery; with inside velvety and outside satiny.
*Shape.*—Outer—roundish; scalloped with 1 notch. Intermediate—obovate; sometimes with 1 notch. Inner—roundish; irregular with 1 notch.

This description of a newly opened flower was made from a rose grown outdoors in the month of June, at West Grove, Pennsylvania, U. S. A.

*Color.*—Outer petal: outside surface—Rose Red, Plate XII, shading to Tyrian Pink, Plate XII near base and to white at base; inside surface—Spectrum Red, Plate I, shading to a narrow zone of Tyrian Pink, Plate XII, with Pale Glass Green, Plate XXXI at base. Intermediate petal: Outside surface—Rose Red, Plate XII, shading to Rose Color, Plate XII and to white at base; inside surface—Spectrum Red, Plate I, shading to Rose Color, Plate XII, with white at base. Inner petal: outside surface—Rose Red, Plate XII, shading to Deep Rose Pink, Plate XII; Veronese Green, Plate XVIII at base; inside surface—Spectrum Red, Plate I, shading to Rose Color, Plate XII; Buff Pink, Plate XXVIII at base.

This description was made from a rose that was open for three days outdoors in the month of June, at West Grove, Pennsylvania, U. S. A.

*Color.*—Outer petal: outside surface—Rose Red, Plate XII, shading to Deep Rose Pink, Plate XII, with white at base; inside surface—Spectrum Red, Plate I, shading to Rose Color, Plate XII; Pale Smoke Gray, Plate XLVI at base. Inner Petal: outside surface—Rose Red, Plate XII, shading to Rose Color, Plate XII, and to white at base; inside surface—Spectrum Red, Plate I at outer edge, shading to Rose Red, Plate XII, then to Deep Rose Pink, Plate XII, with Pale Vinaceous Lilac, Plate XLIV at base.

*General color effect.*—Newly opened flower—Spectrum Red, Plate I, evenly distributed; center of bloom showing Rose Color, Plate XII. Three days open—An even Spectrum Red, Plate I, shading into Rose Pink, Plate XII at base.

*Behavior.*—Drop off cleanly; fading light pink; affected by hot, dry weather—blooms that are passing maturity bleach out.

*Flower longevity.*—On bush in garden—3 days in June. Cut roses grown outdoors and kept at living-room temperatures—3 days in June.

*Reproductive organs*

Stamens: Medium number; arranged regularly about pistils; mixed with petaloids.

Filaments: Many; most with anthers; medium length; white at base; reddish towards anthers.

Anthers: All open at once; medium size; occasionally an anther fused with a petaloid. Color—reddish-brown.

Pollen: Abundant. Color—gold.

Pistils: Medium number.

Styles: Uneven; medium length; thin, bunched.

Stigma: Color—white.

Ovaries: All enclosed in calyx.

Hips: Medium length; ovoid, with inconspicuous neck; smooth; walls thick. Color—Biscay Green, Plate XVII at rear, to Brick Red, Plate XIII at front.

Sepals: Moderately long; straight; permanent.

Seeds: Medium number; medium size.

*Plant*

Foliage:

*Leaves.*—Compound of 5 leaflets; normal abundance; medium size; moderately thin; leathery.

*Leaflets.*—Shape—oval, with apex acute; base round; margin simply serrate.

*Color.* — Mature: upper surface — Cedar Green, Plate VI; under surface—Chromium Green, Plate XXXI. Young: upper surface—Haematite Red, Plate XXVII; under surface—Vandyke Red, Plate XIII.

*Rachis* (the supporting stem of the compound leaf).—Medium caliper. Upper side—grooved; hairy. Under side—smooth.

*Stipules.*—Medium length; medium width; with medium length points turning out at an angle of 45°.

*Disease.*—Resistant to blackspot to about the same degree as average Floribundas, as determined by comparison with other varieties grown under comparable cultural conditions at West Grove, Pennsylvania, U. S. A.

Growth:

*Habit.*—Bushy; upright; much-branched.

*Growth.*—Free.

*Canes.*—Light to medium.

*Main stems.*—Color—Light Elm Green, Plate XVII. Thorns—many; medium length; hooked downward; with medium-long, narrow base. Prickles—several. Color—bronze. Hairs—None.

*Branches.*—Color—Chromium Green, Plate XXXII. Thorns—several; medium length; hooked slightly; pointed downward at a slight angle; medium length, narrow base. Prickles—several. Color—bronze. Hairs—none.

*New shoots.*—Color—pale red, dotted light green. Thorns—many; medium length; straight; with long, narrow, oval base. Prickles — several. Color — reddish. Hairs—none.

I claim:

A new and distinct variety of rose plant of the hybrid polyantha class, substantially as herein shown and described, characterized particularly as to novelty by its brilliant Flame-Rose general color tonality and by its exceptional utility for cut-flower production under glass.

No references cited.